United States Patent
Dow et al.

(10) Patent No.: US 7,368,122 B1
(45) Date of Patent: May 6, 2008

(54) SKIN CREAM

(75) Inventors: Gordon J. Dow, Santa Rosa, CA (US); Kevin Bean, Santa Rosa, CA (US)

(73) Assignee: Dow Pharmaceutical Sciences, Petaluma, CA (US)

( * ) Notice: Subject to any disclaimer, the term of this patent is extended or adjusted under 35 U.S.C. 154(b) by 0 days.

(21) Appl. No.: 10/094,534

(22) Filed: Mar. 8, 2002

(51) Int. Cl.
  *A01N 25/24* (2006.01)
  *A61K 31/74* (2006.01)
(52) U.S. Cl. .................................... 424/407; 424/78.03
(58) Field of Classification Search ................ 424/407, 424/78.03; 514/937
See application file for complete search history.

(56) References Cited

U.S. PATENT DOCUMENTS

| | | | |
|---|---|---|---|
| 4,552,755 A | 11/1985 | Randen | |
| 5,004,598 A | 4/1991 | Lochhead et al. | |
| 5,073,372 A * | 12/1991 | Turner et al. | 424/401 |
| 5,236,710 A | 8/1993 | Guerrero et al. | |
| 5,582,832 A * | 12/1996 | Pillai et al. | 424/401 |
| 5,827,920 A * | 10/1998 | Watanabe et al. | 524/833 |
| 5,863,544 A * | 1/1999 | Willcox et al. | 424/401 |
| 5,928,632 A | 7/1999 | Reusch | |
| 5,976,555 A * | 11/1999 | Liu et al. | 424/401 |
| 6,033,647 A * | 3/2000 | Touzan et al. | 424/45 |
| 6,093,408 A * | 7/2000 | Hasenoehrl et al. | 424/401 |
| 6,106,848 A | 8/2000 | Preuilh et al. | |
| 6,333,039 B1 * | 12/2001 | Fendler et al. | 424/401 |
| 6,517,847 B2 * | 2/2003 | Dow et al. | 424/401 |
| 2002/0098218 A1 * | 7/2002 | Zhuang et al. | 424/40 |

OTHER PUBLICATIONS

BF Goodrich, Polymers for Personal Care, "Skin care products formulated with Pemulen® Polymeric emulfiers", TDS-117 (Apr. 1994).
BF Goodrich, Polymers for Personal Care, TDS-114 (May 1998).
Abstract, "The Composition of the Ceramides from Human Stratum Corneum and from Comedones", J. Invest. Dermatol, May 1985, pp. 410-412.
Abstract, "Metabolism of linoleic acid and other essential fatty acids in the epidermis of the rat", Biochim Biophys Acta, 834(3):429-36 (May 1985).
Abstract, "Sensitivity of staphylococci to fatty acids; novel inactivation of linoleic acid by serum", J. Med. Microbiol., 14(1):41-9 (Feb. 1981).
Abstract, "Water evaporation rates from a model of stratum corneum lipids", J. Pharm. Sci., 7(8):639-43 (Aug. 1989).
Abstract, "Incorporation of 14C-linoleic acid in cerebrosides of psoriatic and normal human skin", Arch Dermatol Res, 270(4):441-4 (1981).
Abstract, "Possible role or squalene and its peroxide of the sebum in the occurrence of sunburn and protection from the damage caused by U.V. irradiation", Toxicol Sci, 9(2):151-9 (May 1984).
Abstract, "Identification, isolation and characterization of epidermal lipids containing linoleic acid", Biochim Biophys Acta, 834(3):419-28 (May 1985).
D-D Chemco, Inc. "Oils of Aloha—The Beauty of Hawaii" (1999).
Speiser, K, et al., "Hemp Seed Oil, The Wonder Oil for the New Millenium", Happi, 106-109 (Jun. 1999).
Dow Chemical Company, "Methocel Cellulose Ethers Technical Handbook" (Sep. 1996).
Abstract, "Linoleic acid in hypertrophic scars", Burns Incl Therm Inj, 9(1):7-12 (Sep. 1982).
Abstract, "Essential fatty acids and epidermal integrity", Arch Dermatol, 123(10):1381-4 (Oct. 1987).
Abstract, "Effect of essential fatty acid deficiency on cutaneous sterol synthesis", J Invest Dermatol, 87(5):588-91 (Nov. 1986).
Abstract, "Murine keratinocyte cultures grown at the air/medium interface synthesize stratum corneum lipids and "recycle" linoleate during differentiation", J Invest Dermatol, 93(1):10-7 (Jul. 1989).
Abstract, "Effect of mineral oil and linoleic-acid -containing emulsions on the skin vapour loss of sodium-lauryl-sulphate-induced irritant skin reactions", Contact Dermatitis, 20(2):93-7 (Feb. 1989).
Abstract, Fatty acids of acylceramides from comdeones and from the skin surface of acne patients and control subjects, J Invest Dermatol, 90(3):350-3 (Mar. 1988).
Abstract, "Conversion of linoleic acid and arachidonic acid by skin epidermal lipoxygenases", Biochim Biophys Acta, 921(1):135-41 (Sep. 1987).
Abstract, "Essential fatty acids and acne", J Am Acad Dermatol, 14(2 pt 1):221-5 (Feb. 1986).
Borage Website (URL unknown), "Borage, . . . New . . . a break-through product line for dry skin that just won't go away" (Sep. 21, 1999).

* cited by examiner

Primary Examiner—Sreeni Padmanabhan
Assistant Examiner—Yong S. Chong
(74) Attorney, Agent, or Firm—Howard Eisenberg, Esq.

(57) ABSTRACT

An emulsion for topical application to the skin containing a high molecular weight emulsifier and substantially no emulsifiers of a molecular weight less than 100 kD. The emulsion may be used to prevent or treat dermatoses and may additionally contain pharmaceutically active ingredients.

50 Claims, No Drawings

SKIN CREAM

FIELD OF THE INVENTION

The invention pertains to the field of emulsions for treating and protecting skin or for use as a vehicle to deliver pharmacologic agents topically to treat diseases of the skin, particularly the skin of the hands.

BACKGROUND OF THE INVENTION

Hand dermatitis may result from exposure to numerous environmental irritants, including soaps, detergents, chemicals, frequent hand washing, and continual or repeated glove use. Susceptible individuals are predisposed to developing dermatitis due to the sensitive nature of their skin, such as atopic eczema.

Hand dermatitis can be managed by (1) using topical steroids (e.g., hydrocortisone), (2) using protective gloves to avoid contact with irritants, (3) identifying and reducing exposure to irritants and allergens, and (4) keeping the hands consistently lubricated with emollients.

Commercial products to treat dermatitis are frequently emulsions, especially semisolid emulsions (i.e., creams). Creams are the most popular delivery system for topical drugs because of cosmetic and aesthetic properties. Emulsifiers, typically surfactants that penetrate the stratum corneum and disrupt the barrier, are required ingredients of emulsions and typically at least one and preferably two low molecular weight emulsifiers are used in commercial creams.

It has been established that the ingredients present in topical therapeutic treatments (i.e., creams, lotions, and ointments) may prevent healing or may even worsen the damaged skin of the hands. The culprit chemicals have been preservatives or excipients to which the individual had an allergic contact dermatitis. Frequent hand washings can over-dry and cause chapping of sensitive hands. In order to counteract this adverse effect of frequent exposure to soap and water, moisturizers and lubricants are commonly used.

Irritating materials such as detergents are commonly present as emulsifiers in topical creams and lotions. These materials provide an additive or synergistic effect to increase the potential for irritation of the treated skin caused by frequent skin washing or topical pharmacologic treatment of irritated or potentially irritated skin. Moreover, many therapeutic agents, such as retinoic acid, benzoyl peroxide, sunscreens, and anti-perspirants, which are incorporated into creams and lotions to treat skin disease, are themselves irritating to skin.

A significant need exists for an emulsion that can be utilized as a moisturizer, as a protectant, or as a vehicle for potentially irritating therapeutic agents that will reduce, or at least not potentiate, irritation of sensitive or diseased skin. Such an emulsion should be stable, cosmetically elegant, compatible with a wide variety of drug substances, and most importantly be non-irritating to sensitive or dermatitic skin.

SUMMARY OF THE INVENTION

In one embodiment, the invention is a non-irritating emulsion that may be used for treating, protecting or preventing dermatitic skin, especially eczema, or as a vehicle to deliver a pharmacological agent or drug topically to treat or prevent dermatitis.

The emulsion of the invention is suitable for formulation as a therapeutic emulsion such as a semi-solid like a cream or a flowable fluid like a lotion. It is physically and chemically stable, non-irritating to dermatitic skin, and compatible with a variety of pharmaceutical active ingredients.

The emulsion of the invention, and formulations containing the emulsion of the invention, may be used to prevent and to treat dermatoses of various types. For example, the invention may be used to prevent or treat hand dermatitis or eczema, atopic dermatitis, psoriasis, rosacea, steroid-responsive dermatoses, pruritis, and xerosis.

The emulsion of the invention may further be used as a delivery vehicle for the topical delivery of pharmaceutically active ingredients to mucous membranes, an epithelial tissue that lacks the protective stratum corneum found as the outer layer of the skin. Such delicate mucous membrane tissues include the vagina, the oral mucosa, the ano-rectal mucosa, the nasal mucosa, and the ear canal.

The emulsion of the invention may be utilized to provide a bland, non-irritating topical delivery system for irritating active drug substances such as retinoic acid, benzoyl peroxide, sunscreens, and antiperspirants.

The emulsion of the invention may be utilized to provide a delivery vehicle for topically administered corticosteroids or immune modulating drugs. Corticosteroids may mask vehicle irritation due to the pharmacological effect of the corticosteroid. Thus, use of the emulsion of the invention in conjunction with such topical corticosteroid therapy may increase the overall effectiveness of topical corticosteroids, especially in situations of chronic or repeated use.

In another embodiment, the invention is a method for preventing or treating a dermatosis, such as dermatitis. According to this embodiment of the invention, the emulsion of the invention is applied to the skin of an individual in need of such application. These individuals include those individuals suffering from a dermatosis, such as a dermatitis which may be a hand dermatitis, and those individuals with sensitive skin that is susceptible to developing a dermatosis.

Additional embodiments of the invention are described below or will be evident to one skilled in the art in view of the description provided in this application.

DETAILED DESCRIPTION OF THE INVENTION

It has been discovered that an emulsion containing a low molecular weight surfactant, especially those that are anionic, as an emulsifier can cause or contribute to the development or worsening of contact skin irritation. The emulsion of the invention utilizes one or more high molecular weight emulsifiers, preferably polymeric in nature, and most preferably anionic type, and contains no, or substantially no, low molecular weight emulsifiers. Although anionic emulsifiers are generally known to be more irritating than non-ionic emulsifiers, the invention achieves non-irritating formulations with emulsifiers of the anionic type. The high molecular weight polymeric emulsifiers are those that do not significantly penetrate into the skin's protective stratum corneum.

The emulsions according to the invention are stable, cosmetically elegant, compatible with a wide variety of drug substances and, most importantly, are non-irritating to dermatitic skin. Even with impaired barrier function of dermatitic skin or mucous membranes, which are devoid of the stratum corneum barrier of the skin, the high molecular weight emulsifiers contained in the emulsion of the invention do not penetrate into the epithelial cells in sufficient concentration to cause the signs and symptoms of irritation, cause a sub-clinical irritation, or enhance the irritation caused by irritating drug substances. Unlike prior art emulsions used for prophylaxis or therapy for dermatoses or for delivery vehicles for topical therapeutic agents, the emulsion of the invention does not cause any measurable irritation to skin, even to skin that is diseased or that has disrupted barrier function.

It was surprisingly discovered that the emulsions of the invention, especially those containing silicone oil, such as dimethicone or cyclomethicone, in combination with fatty alcohols and oleaginous materials such as sunflower seed oil, petrolatum, and microcrystalline wax, are stable, even without the use of low molecular weight non-ionic or ionic surfactants.

It was also surprisingly discovered that such stable emulsions could be obtained without the use of low molecular weight emulsifiers as primary or secondary emulsifiers or co-emulsifiers. As disclosed in U.S. Pat. No. 5,004,598, emulsions made with carbomer copolymer resins are unstable.

It was also surprisingly discovered that cosmetically elegant emulsion formulations could be created using only high molecular weight polymeric emulsifiers.

It was further discovered that, with the emulsions of the invention, latex glove incompatibility could be avoided, while at the same time achieving effective emolliency and skin protective properties by carefully selecting the qualitative and quantitative composition of the oil phase.

It was also surprisingly discovered that the emulsions of the invention are slow breaking, in contrast to what is reported in U.S. Pat. No. 5,004,598 with emulsions containing acrylates/C10-C30 alkyl acrylate crosspolymer as the emulsifier and lacking conventional surfactants. Such emulsions are reported to break instantaneously upon contact with skin. Such rapid break is not seen with the emulsions according to the present invention. In contrast with the prior art, the emulsions of the invention do not break upon contact with the skin, and do not break within the first 10 seconds, even upon rubbing into the skin. Preferably, the emulsions of the invention display no noticeable break, even after several minutes of skin contact. This lack of instantaneous breaking of the emulsions of the invention upon contact with skin is obtained even though the emulsions of the invention lack surfactants and may not include slightly surface active film formers such as hydroxypropyl methylcellulose or poloxamer 181, 182, or 183.

The high molecular weight emulsifiers suitable for the emulsion of the invention are polymeric emulsifiers having a molecular weight of 100,000 or more, preferably 1,000,000 or more, and containing both hydrophilic and hydrophobic moieties. The high molecular weight emulsifiers of our invention are primary emulsifiers that form heat-stable emulsions without the use of any low molecular weight primary emulsifiers. The preferred high-molecular weight emulsifiers are acrylates/C10-C30 alkyl acrylate crosspolymer, such as Pemulen TR1, Pemulen TR-2, and carbomers such as Carbopol 1342 and Carbopol 1382 (B.F. Goodrich, Cleveland, OH). The operative concentration of the high molecular weight polymeric emulsifiers is from about 0.05 to about 2.5%, the preferred concentration is from about 0.05 to about 0.75% and the most preferred concentration is from about 0.1 to about 0.5% by weight total of one or more such emulsifiers. The preferred emulsion contains two polymeric emulsifiers together to produce the best quality emulsion that is not fast breaking. The preferred polymeric emulsifiers in accordance with the invention are Carbopol 1382 and Pemulen TR-1. The preferred ratio of these polymeric emulsifiers is about 1:5 to 1:1 (Pemulen TR-1: Carbopol 1382).

Low molecular weight emulsifiers for prior art skin use emulsions are used at concentrations typically from 0.5% to 10%, more typically from 1% to 7% and most typically from 2% to 5%. One advantage of the emulsion of the present invention is in the lower total concentration of emulsifier required to make and maintain the emulsion stable as compared with conventional emulsions. The emulsions of the invention typically utilize a concentration of emulsifier less than 0.5% high molecular weight polymeric emulsifiers and in its most preferred embodiment from 0.03 to 0.3% emulsifier by weight. Therefore, not only is a diseased epithelium exposed to a different type of emulsifier than in conventional therapeutic emulsions, but the amount of emulsifier is also lower.

The emulsion of the invention is particularly useful in the management of hand dermatitis. Additional utilities for the emulsion of the invention include the treatment of eczema (including atopic eczema) and other epithelial (skin and mucous membrane) conditions. A further application is as a non-irritating emulsion carrier for topical drugs (e.g. betamethasone dipropionate and calcipotriol) to treat psoriasis, which is subject to exacerbation, from irritant contact materials. Psoriasis is a disease that can be worsened by irritation or trauma to the skin, one result of which is the Koebner effect or spreading of the dermatitis over an area of traumatized skin. The skin of psoriatic lesions is well known to have an impaired barrier function. Thus, psoriasis is another example of dermatitic skin that can benefit from the non-irritating emulsion delivery system of the invention. In contrast to the present invention, conventional emulsions with low molecular weight emulsifiers may worsen or diminish the therapeutic effect of the active drug substance by virtue of chronic mild irritation or subclinical irritation. Even relatively small amounts of low molecular weight emulsifiers of the anionic type can cause sub-clinical or clinical irritation with repeated use.

Irritating materials such as detergents commonly used as emulsifiers in topical creams and lotions cause an additive or synergistic effect on the irritation of treated skin that is caused by irritating or potentially irritating active drug substances. Thus, another aspect of the inventions is as a topical carrier for drug substances known to be irritating, such as tretinoin and benzoyl peroxide, antiperspirants and sunscreens.

The emulsion of the invention avoids the counterproductive low-grade, mild or sub-clinical irritation caused by typical emulsions, which irritation is detrimental to the healing process of irritated or diseased skin. Additionally, in one embodiment the emulsion of the invention is suitable for use with moisturizers, skin protectants or therapeutic agents (e.g., antibiotic creams) in individuals who must wear rubber or plastic gloves (e.g., medical examination gloves) for their work. The glove creates an occlusive effect on the hands, which exacerbates the effects of irritant materials. The emulsion of the invention overcomes this problem of conventional (low-molecular weight) emulsifiers causing additional irritation in glove wearers.

In this preferred embodiment, the emulsion of the invention is compatible with latex, vinyl, nitrile and other medical examination gloves. Such emulsion compositions, in accordance with the invention, have an oil phase comprised of not more than about 30% of the total formula weight, preferably not more than about 20%, and most preferably not more than about 15%.

Preferably, but not necessarily, if to be used by individuals who wear gloves, the oil phase composition is free of any petroleum-based components, including mineral oil, alkanes, and alkenes, that are liquid at room temperature. Thus, the oil phase of the preferred emulsion of the invention contains primarily or preferably entirely of solid and semi-solid materials at room temperature, except for silicones and triglycerides, which may be liquids at room temperature.

Atopic eczema, common among infants and children, is another example where overexposure to irritants in the carrier for the medicinal agent may be beneficially overcome by our invention. Patients with atopic eczema have an impaired skin barrier function and irritating topical materials easily worsen their skin condition. The emulsions of the invention maximize therapeutic outcome by eliminating unwanted irritancy, especially sub-clinical irritant effects, from conventional low-molecular weight surfactants used as emulsifiers. A cream with a fatty acid triglyceride which is rich in essential fatty acids and cholesterol provides moisturization and barrier repair properties, either alone or as adjunctive treatment, and also as a follow-up therapy after topical corticosteroids or after immune modulating drugs such as tacrolimus. Also, tacrolimus is useful as the active ingredient to treat atopic dermatitis in the non-irritating emulsion vehicle of the present invention.

Topical corticosteroids represent the most widely used class of topical medicinal agents. Corticosteroids vary in chemical structure, strength and potency yet as a class have common pharmacological properties, e.g., antipruritic and anti-inflammatory actions. Topical steroids are used for both acute and chronic steroid responsive dermatitis. The irritation of prior art low molecular weight emulsifiers are at times outwardly masked by the anti-inflammatory corticosteroid effect. Yet, the chronic subclinical insult of these low molecular weight emulsifiers diminishes the therapeutic response which prevents complete resolution of a dermatosis in the same way that allergic contact dermatitis in response to an excipient in a steroid cream has been reported to do.

In one embodiment, the emulsion of the invention includes a fatty acid triglyceride in which the fatty acid component is rich in essential fatty acids, that is it contains one or more essential fatty acids (EFAs), such as linoleic acid or linolenic acid. This embodiment is especially well suited for the treatment of eczema, including atopic dermatitis and hand eczema. Examples of suitable essential fatty acids include linoleic acid and linolenic acid. Suitable triglycerides for this embodiment of the emulsion of the invention include, but are not limited to, kukui nut oil, borage oil, evening primrose oil, soy oil, sesame oil, sunflower seed oil, hemp seed oil, and black currant oil. Sunflower seed oil, also know simply as sunflower oil, is the preferred source of such fatty acid triglycerides because of reasonably high EFA content, plentiful supply and reasonable cost.

If present, the concentration of EFA-rich fatty acid triglycerides suitable for the emulsion of the invention is 1% to 50% of the formula weight. The preferred amount is 2% to 30% and the most preferred concentration range is 3% to 15% by weight of the formula. It is undesirable to use pure fatty acid triglycerides on the skin as investigators have reported the disadvantages of low cosmetic elegance, difficulty in application to the skin due to fluidity, and absence of water to provide natural hydration of the stratum corneum. The inclusion of safflower oil, for example in the invention provides moisturization and assists in healing of the affected skin.

In another preferred embodiment, the emulsion of the invention includes cholesterol at a level of 0.05% to 10% by weight, preferably 0.1% to 3%, and glycerin and/or sorbitol at a level of 1% to 20%, preferably 3% to 10%. There is a combined soothing, healing, protective, and skin barrier enhancement effect of the combination of cholesterol, glycerin and EFA-rich fatty acid triglycerides in a surfactant-free emulsion comprising one or more polymeric emulsifiers in accordance with the invention.

Another useful application of the invention is for the delivery of anti-aging drugs and cosmeceuticals to sensitive areas such as the face and other sun-exposed skin areas. Examples of such active ingredients are Vitamin E and its derivatives, Vitamin C and its derivatives, $N^6$-furfuryladenine, retinol and other antioxidant or free-radical scavengers. It is particularly useful to have a carrier that is essentially free of potential sub-clinical irritation when treating sun-exposed or sun-damaged skin over an extended time period. The invention provides significant benefit in this application as a carrier for drugs and cosmeceuticals indicated for treating or preventing skin aging.

A further aspect of the invention is as an emulsion to deliver isopropyl myristate to the skin to maintain individuals with atopic dermatitis or hand dermatitis. Reference is made to U.S. Pat. No. 5,886,038. The concentrations of isopropyl myristate useful for this embodiment of the invention range from about 15% to 95% of the formulation by weight. The preferred amount of isopropyl myristate is from about 15% to 75% and the most preferred amount is from about 40% to 60%. The most preferred composition and method for treating atopic dermatitis and hand dermatitis utilizing the invention involves the combination of isopropyl myristate with a high EFA-containing triglyceride such as sunflower oil. The ratio of isopropyl myristate to the high-EFA-containing triglyceride is preferably about 10:1 to 1:1.

The invention is illustrated by the following non-limiting examples.

In these examples, proprietary products were utilized as follows: Carbopol 1382 and Pemulen (BF Goodrich, Cleveland, Ohio), also known by the name acrylates/C10-C30 alkyl acrylate crosspolymer, and Dow Corning 2503, a silicone wax.

EXAMPLE 1

Hand Dermatitis Cream—A moisturizer for treating hand dermatitis especially at nighttime with the active ingredients to help healing being sunflower seed oil and cholesterol

| COMPONENT | % w/w |
| --- | --- |
| Sunflower Seed Oil | 3.0 |
| Cholesterol | 0.2 |
| Cyclomethicone | 0.3 |
| Stearic Acid | 3.0 |
| Stearyl Alcohol | 3.0 |
| Cetyl Alcohol | 1.0 |
| White Petrolatum | 5.0 |
| Carbopol 1382 | 0.1 |
| Pemulen TR-1 | 0.2 |
| Xanthan Gum | 0.1 |
| Glycerin | 6.0 |
| Sorbitol Solution, 70% | 3.0 |

-continued

| COMPONENT | % w/w |
|---|---|
| Tocopherol (Vitamin E) | 0.005 |
| Methylparaben | 0.2 |
| Propylparaben | 0.03 |
| Tromethamine | qs pH 5.0 |
| Purified Water | QSAD 100 |

The following procedure was used to produce a laboratory batch according to the formula in the previous table:

a) Combine Purified Water, Tromethamine, Glycerin and Sorbitol Solution in beaker. Add parabens and Sunflower Seed Oil. Heat to 60-70° C.
b) Combine Stearyl Alcohol, Cetyl Alcohol, Stearic Acid, White Petrolatum, Cholesterol, Cyclomethicone and Tocopherol in beaker. Heat to 60-70° C. Add Carbopol 1382, Xanthan Gum and Pemulen TR-1. Mix to disperse.
c) Add the materials from step b) to step a) at 60-70° C. with rapid propeller mixing. Mix until smooth, homogeneous emulsion forms.
d) Continue mixing while cooling to room temperature.

EXAMPLE 2

Hand Dermatitis Cream—A moisturizing protectant cream for treating hand dermatitis based on dimethicone, silicone wax, and cholesterol as the active ingredients

| COMPONENT | % w/w |
|---|---|
| Dimethicone | 0.2 |
| Dow Corning 2503 Wax | 3.0 |
| Cholesterol | 0.2 |
| Stearic Acid | 3.0 |
| Stearyl Alcohol | 5.0 |
| Cetyl Alcohol | 1.0 |
| White Petrolatum | 5.0 |
| Carbopol 1382 | 0.1 |
| Pemulen TR-1 | 0.2 |
| Xanthan gum | 0.1 |
| Glycerin | 6.0 |
| Sorbitol Solution, 70% | 3.0 |
| Benzyl Alcohol | 1.2 |
| Tromethamine | qs pH 5.0 |
| Purified Water | QSAD 100 | a) Combine Purified Water, Tromethamine, Glycerin and Sorbitol Solution in beaker. Heat to 60-70° C.
b) Combine Dow Corning 2503 Wax, Stearyl Alcohol, Cetyl Alcohol, Stearic Acid, White Petrolatum, Cholesterol, and Dimethicone in beaker. Heat to 60-70° C. Add Carbopol 1382, Xanthan Gum and Pemulen TR-1. Mix to disperse.
c) Add the materials from step b) to step a) at 60-70° C. with rapid propeller mixing. Add Benzyl Alcohol and mix until smooth, homogeneous emulsion forms.
d) Continue mixing while cooling to room temperature.

EXAMPLE 3

Hand Dermatitis Lotion—A lotion for hand dermatitis

This embodiment of the invention is emollient and moisturizing and aids in skin barrier restoration, yet it is cosmetically elegant enough for daytime use.

| COMPONENT | % w/w |
|---|---|
| Cyclomethicone | 0.3 |
| Sunflower Seed Oil | 3.0 |
| Stearic Acid | 4.0 |
| Stearyl Alcohol | 0.50 |
| Carbopol 1382 | 0.05 |
| Pemulen TR-1 | 0.2 |
| Xanthan Gum | 0.1 |
| Glycerin | 2.5 |
| Sorbitol Solution, 70% | 2.0 |
| Methylparaben | 0.2 |
| Propylparaben | 0.03 |
| Tocopherol | 0.005 |
| Tromethamine (10% aqueous) | qs pH 5.2 |
| Purified Water | QSAD 100 | a) Combine Purified Water, Tromethamine, Glycerin and Sorbitol Solution in beaker. Add Parabens and Sunflower Seed Oil. Heat to 60-70° C.
b) Combine Stearyl Alcohol, Stearic Acid and Dimethicone in beaker. Heat to 60-70° C. Add Carbopol 1382, Xanthan Gum and Pemulen (TR-1). Mix to disperse.
c) Add the materials from step b) to step a) at 60-70° C. with rapid propeller mixing. Mix until a smooth, homogeneous emulsion forms.
d) Continue mixing while cooling to room temperature.

EXAMPLE 4

Moisturizing Hand Protectant Lotion—A protectant lotion with moisturizing properties that is especially well suited for hand dermatitis

| COMPONENT | % w/w |
|---|---|
| Dimethicone | 0.2 |
| Dow Corning 2503 Wax | 3.0 |
| Stearic Acid | 4.0 |
| Stearyl Alcohol | 0.50 |
| Carbopol 1382 | 0.05 |
| Pemulen TR-1 | 0.2 |
| Xanthan Gum | 0.1 |
| Glycerin | 2.5 |
| Sorbitol Solution, 70% | 2.0 |
| Benzyl Alcohol | 1.2 |
| Tromethamine (10% aqueous) | qs pH 5.2 |
| Purified Water | QSAD 100 | a) Combine and mix Purified Water, Tromethamine, Glycerin and Sorbitol Solution in beaker. Heat to 60-70° C.
b) Combine Dow Corning 2503 Wax, Stearyl Alcohol, Stearic Acid and Dimethicone in beaker. Heat to 60-70° C. Add Carbopol 1382, Xanthan Gum and Pemulen TR-1. Mix to disperse.
c) Add the materials from step b) to step a) at 60-70° C. with rapid propeller mixing. Add Benzyl Alcohol and mix until smooth, homogeneous emulsion forms.
d) Continue mixing while cooling to room temperature.

EXAMPLE 5

Antipruritic Cream

Itchy skin is frequently broken due to scratching, and subject to stinging and burning. The emulsion of the invention is particularly useful for the delivery of antipruritic drug substances, such as benzyl alcohol, camphor, and menthol.

| COMPONENT | % w/w |
| --- | --- |
| Benzyl Alcohol (Active Ingredient) | 10.0 |
| Camphor (Active Ingredient) | 0.1 |
| Menthol (Active Ingredient) | 0.1 |
| Isopropyl Myristate | 1.5 |
| Microcrystalline Wax | 3.0 |
| Stearic Acid | 6.0 |
| Stearyl Alcohol | 5.0 |
| Cetyl Alcohol | 1.0 |
| Cholesterol | 0.2 |
| White Petrolatum | 5.0 |
| Carbopol 1382 | 0.1 |
| Pemulen (TR-1) | 0.2 |
| Polyethylene Glycol 400 | 4.0 |
| Glycerin | 6.0 |
| Tromethamine | qs pH 6.0 |
| Purified Water | QSAD 100 | a) Combine and mix Purified Water, Tromethamine, Glycerin and Polyethylene Glycol in beaker. Heat to 60-70° C.
b) Combine Stearyl Alcohol, Cetyl Alcohol, Stearic Acid, White Petrolatum, Cholesterol, Isopropyl Myristate, and Microcrystalline Wax in beaker. Heat to 60-70° C. Add Carbopol 1382 and Pemulen(TR-1). Mix to disperse. Add the materials from step b) to step a) at 60-70° C. with rapid propeller mixing. Dissolve the Camphor and Menthol in the Benzoyl Alcohol with stirring. Add Benzyl Alcohol solution to Step c) and mix until smooth, homogeneous emulsion forms.
e) Continue mixing while cooling to room temperature.

EXAMPLE 6

Hydrocortisone Cream—for treating the inflammatory aspects of dermatitis

| COMPONENT | % w/w |
| --- | --- |
| Hydrocortisone (micronized) | 1.0 |
| Microcrystalline Wax | 1.0 |
| White Wax | 3.0 |
| Stearic Acid | 3.0 |
| Stearyl Alcohol | 5.0 |
| Carbomer 1382 | 0.1 |
| Pemulen TR-1 | 0.2 |
| Propylene Glycol | 6.0 |
| Benzyl Alcohol | 1.2 |
| Tromethamine (10% aqueous) | qs pH 5.5 |
| Cetyl Alcohol | 1.0 |
| White Petrolatum | 5.0 |
| Purified Water | QSAD 100 | a) Combine one-third of the Purified Water, Tromethamine, and Propylene Glycol in beaker. Disperse Hydrocortisone into aqueous blend with homogenizing mixer. Add the balance of the Purified Water and mix well. Heat to 60-70° C.
b) Combine Stearyl Alcohol, Stearic Acid, White Petrolatum, Cetyl Alcohol, Microcrystalline Wax and White Wax in beaker. Heat to 60-70° C. Add Carbopol 1382 and Pemulen TR-1. Mix to disperse.
c) Add the materials from step b) to step a) at 60-70° C. with rapid propeller mixing. Add Benzyl Alcohol and mix until smooth, homogeneous emulsion forms.
d) Continue mixing while cooling to room temperature.

EXAMPLE 7

Tretinoin Cream

Tretinoin (all trans retinoic acid) is inherently irritating to the skin. The emulsion of the invention delivers Tretinoin in a bland, non-irritating vehicle that will not add to or be synergistic with the Tretinoin skin irritation.

| COMPONENT | % w/w |
| --- | --- |
| Retinoic Acid | 0.05 |
| Dimethicone | 0.3 |
| White Wax | 3.0 |
| Stearic Acid | 5.0 |
| Stearyl Alcohol | 4.0 |
| Cetyl Alcohol | 2.0 |
| White Petrolatum | 5.0 |
| Carbomer 1382 | 0.1 |
| Pemulen (TR-1) | 0.2 |
| Glycerin | 6.0 |
| Methylparaben | 0.2 |
| Propylparaben | 0.03 |
| Tromethamine (10% aqueous) | qs pH 5.0 |
| Purified Water | QSAD 100 | a) Combine one-third of the Purified Water, Tromethamine and Glycerin in beaker. Disperse Retinoic Acid into aqueous blend with homogenizing mixer. Add the balance of the Purified Water and mix well. Heat to 60-70° C. Add the Methylparaben and Propylparaben and mix well to dissolve.
b) Combine Stearyl Alcohol, Stearic Acid, White Petrolatum, Cetyl Alcohol, White Wax and Dimethicone in beaker. Heat to 60-70° C. Add Carbopol 1382 and Pemulen TR-1. Mix to disperse.
c) Add the materials from step b) to step a) at 60-70° C. with rapid propeller mixing. Mix until smooth, homogeneous emulsion forms.
d) Continue mixing while cooling to room temperature.

EXAMPLE 8

Benzoyl Peroxide Emulsion

Benzoyl Peroxide, an effective acne medication, is irritating to many patients, particularly at higher concentrations. The non-irritating vehicle of the invention avoids an additive or synergistic effect of Benzoyl Peroxide due to subclinical emulsifier irritation.

| COMPONENT | % w/w |
| --- | --- |
| Benzoyl Peroxide, micronized | 10.0 |
| Dimethicone | 0.2 |

-continued

| COMPONENT | % w/w |
|---|---|
| White Wax | 3.0 |
| Stearic Acid | 5.0 |
| Stearyl Alcohol | 5.0 |
| Cetyl Alcohol | 1.0 |
| Carbomer 1382 | 0.1 |
| Pemulen (TR-1) | 0.2 |
| Propylene Glycol | 3.0 |
| Methylparaben | 0.20 |
| Propylparaben | 0.03 |
| Tromethamine (10% aqueous) | qs pH 6.0 |
| Purified Water | QSAD 100 | a) Combine Purified Water, Tromethamine and Propylene Glycol in beaker. Disperse Benzoyl Peroxide into aqueous blend with homogenizing mixer. Heat to 60-70° C.

b) Combine Stearyl Alcohol, Stearic Acid, Cetyl Alcohol, White Wax and Dimethicone in beaker. Heat to 60-70° C. Add Carbopol 1382 and Pemulen TR-1. Mix to disperse.

c) Add the materials from step b) to step a) at 60-70° C. with rapid propeller mixing. Mix until smooth, homogeneous emulsion forms.

d) Continue mixing while cooling to room temperature.

EXAMPLE 9

Sunscreen Emulsion

Sunscreens, particularly formulations with high sun protective values, are frequently irritating to the facial skin and eyes. The emulsion vehicle of the invention is a superior way to deliver sunscreen to the exposed skin in a non-irritating carrier.

| COMPONENT | % w/w |
|---|---|
| Benzophenone 3 | 5.0 |
| Octyl Cinnamate | 8.0 |
| Dimethicone | 0.5 |
| Dow Corning 2503 Wax | 2.0 |
| Stearic Acid | 6.0 |
| Stearyl Alcohol | 0.5 |
| Carbomer 1382 | 0.05 |
| Pemulen TR-1 | 0.2 |
| Ethoxydiglycol | 3.0 |
| Benzyl Alcohol | 1.2 |
| Tromethamine (10% aqueous) | qs pH 5.5 |
| Purified Water | QSAD 100 | a) Combine Purified Water, Tromethamine, and Ethoxydiglycol in beaker. Dissolve Benzophenone 3 into mixture. Heat to 60-70° C.

b) Combine Dow Corning 2503 Wax, Stearyl Alcohol, Stearic Acid and Dimethicone in beaker. Heat to 60-70° C. Add Carbopol 1382, and Pemulen TR-1. Mix to disperse.

c) Add the materials from step b) to step a) at 60-70° C. with rapid propeller mixing. Add Benzyl Alcohol and Octyl Cinnamate and continue mixing until smooth, homogeneous emulsion forms.

d) Continue mixing while cooling to room temperature.

EXAMPLE 10

Clindamycin Topical Lotion

Clindamycin Topical Lotion preparation may be beneficially used topically to treat acne and rosacea.

| COMPONENT | % w/w |
|---|---|
| Clindamycin Phosphate | 1.2 |
| Dimethicone | 0.25 |
| White Wax | 3.0 |
| Stearic Acid | 4.0 |
| Cetyl Alcohol | 0.5 |
| Carbomer 1382 | 0.05 |
| Pemulen TR-1 | 0.2 |
| Propylene Glycol | 5.0 |
| Methylparaben | 0.2 |
| Propylparaben | 0.03 |
| Tromethamine (10% aqueous) | qs pH 5.2 |
| Purified Water | QSAD 100 | a) Combine Purified Water, Tromethamine, and Propylene Glycol in beaker. Heat to 60-70° C. Add Methylparaben and Propylparaben and mix vigorously until dissolved.

b) Combine Stearic Acid, White Wax, Cetyl Alcohol and Dimethicone in beaker. Heat to 60-70° C. Add Carbopol 1382 and Pemulen TR-1. Mix to disperse.

c) Add the materials from step b) to step a) at 60-70° C. with rapid propeller mixing. Mix until smooth, homogeneous emulsion forms.

d) Dissolve Clindamycin Phosphate into mixture by mixing well. Continue mixing while cooling to room temperature.

EXAMPLE 11

Moisturizing Urea Lotion

An example of a moisturizing lotion is shown. Urea, the active ingredient, can be irritating. The bland emulsion vehicle of the invention minimizes sensory irritation from topical urea, especially important in eczema patients.

| COMPONENT | % w/w |
|---|---|
| Urea | 10.0 |
| Dimethicone | 0.2 |
| Dow Corning 2503 Wax | 2.5 |
| Stearic Acid | 3.0 |
| Stearyl Alcohol | 0.6 |
| Carbomer 1342 | 0.15 |
| Pemulen TR-1 | 0.2 |
| Glycerin | 5.0 |
| Methylparaben | 0.2 |
| Propylparaben | 0.03 |
| Tromethamine (10% aqueous) | qs pH 5.0 |
| Purified Water | QSAD 100 | a) Combine and mix Purified Water, Tromethamine and Glycerin in beaker. Heat to 60-70° C. Add Methylparaben and Propylparaben and mix well to dissolve.

b) Combine Dow Corning 2503 Wax, Stearyl Alcohol, Stearic Acid and Dimethicone in beaker. Heat to 60-70° C. Add Carbopol 1342 and Pemulen TR-1. Mix to disperse.

c) Add the materials from step b) to step a) at 60-70° C. with rapid propeller mixing. Mix until smooth, homogeneous emulsion forms.

d) Dissolve Urea into mixture. Continue mixing while cooling to room temperature.

EXAMPLE 12

Metronidazole Dermal Lotion

Topical Metronidazole is used topically to treat skin diseases such as rosacea. Patients with rosacea have particularly dry and sensitive skin. The emulsion vehicle of the invention is ideally suited for delivery of topical drugs to treat rosacea.

| COMPONENT | % w/w |
| --- | --- |
| Metronidazole | 0.75 |
| Dimethicone | 0.25 |
| Stearic Acid | 7.5 |
| Stearyl Alcohol | 1.5 |
| Carbomer 1382 | 0.05 |
| Pemulen TR-1 | 0.2 |
| Propylene Glycol | 3.5 |
| Methylparaben | 0.2 |
| Propylparaben | 0.03 |
| Tromethamine (10% aqueous) | qs pH 5.5 |
| Purified Water | QSAD 100 | a) Combine and mix Purified Water, Tromethamine, Propylene Glycol and Metronidazole in beaker. Heat to 60-70° C. Add Methylparaben and Propylparaben and mix well until dissolved.

b) Combine Stearyl Alcohol, Stearic Acid and Dimethicone in beaker. Heat to 60-70° C. Add Carbopol 1382 and Pemulen TR-1. Mix to disperse.

c) Add the materials from step b) to step a) at 60-70° C. with rapid propeller mixing. Mix until smooth, homogeneous emulsion forms.

d) Continue mixing while cooling to room temperature.

EXAMPLE 13

Skin Protectant Lotion with Dimethicone as the active ingredient

| COMPONENT | % w/w |
| --- | --- |
| Dimethicone (Active Ingredient) | 3.0 |
| Stearic Acid | 4.0 |
| Stearyl Alcohol | 2.5 |
| Carbomer 1382 | 0.05 |
| Pemulen TR-1 | 0.2 |
| Glycerin | 2.5 |
| Sorbitol Solution, 70% | 2.0 |
| Benzyl Alcohol | 1.2 |
| Tromethamine (10% aqueous) | qs pH 5.5 |
| Purified Water | QSAD 100 | a) Combine and mix Purified Water, Tromethamine, Glycerin and Sorbitol Solution in beaker. Heat to 60-70° C.

b) Combine Stearyl Alcohol, Stearic Acid and Dimethicone in beaker. Heat to 60-70° C. Add Carbopol 1382 and Pemulen TR-1. Mix to disperse.

c) Add the materials from step b) to step a) at 60-70° C. with rapid propeller mixing. Add Benzyl Alcohol and mix until smooth, homogeneous emulsion forms.

d) Continue mixing while cooling to room temperature.

EXAMPLE 14

Miconazole Vaginal Cream

The vaginal mucosa is sensitive and subject to additive irritant effects. Miconazole Vaginal Cream in a surfactant-free carrier, in accordance with the invention is shown.

| COMPONENT | % w/w |
| --- | --- |
| Miconazole Nitrate, micronized | 1.0 |
| White Wax | 3.0 |
| Stearic Acid | 3.0 |
| Stearyl Alcohol | 5.0 |
| Cetyl Alcohol | 1.5 |
| White Petrolatum | 3.0 |
| Carbomer 1382 | 0.2 |
| Pemulen TR-1 | 0.2 |
| Glycerin | 4.0 |
| Methylparaben | 0.2 |
| Propylparaben | 0.03 |
| Tromethamine (10% aqueous) | qs pH 4.5 |
| Purified Water | QSAD 100 | a) Combine and mix Purified Water and Tromethamine in beaker. Heat to 60-70° C. Dissolve the Methylparaben and Propylparaben with mixing.

b) Combine Stearyl Alcohol, Stearic Acid, White Petrolatum, Cetyl Alcohol and White Wax in beaker. Heat to 60-70° C. Add Carbopol 1382 and Pemulen TR-1. Mix to disperse.

c) Add the materials from step b) to step a) at 60-70° C. with rapid propeller mixing. Mix until smooth, homogeneous emulsion forms. Cool to about 40° C. while continuing to mix. Disperse the Miconazole Nitrate in the Glycerin with homogenizing mixer. Add to Step d) and mix well. Continue mixing while cooling to room temperature.

EXAMPLE 15

Calcipotriol Emulsion—for the treatment of psoriasis

| COMPONENT | % w/w |
| --- | --- |
| Calcipotriol, Micronized | 0.005 |
| Mineral Oil | 2.0 |
| Microcrystalline Wax | 3.0 |
| Stearic Acid | 3.0 |
| Stearyl Alcohol | 5.0 |
| Cetyl Alcohol | 2.0 |
| White Petrolatum | 8.0 |
| Carbomer 1382 | 0.1 |
| Pemulen TR-1 | 0.2 |
| Glycerin | 6.0 |
| Benzyl Alcohol | 1.2 |
| Tromethamine (10% aqueous) | qs pH 5.0 |
| Purified Water | QSAD 100 | a) Combine and mix Purified Water and Tromethamine in beaker. Heat to 60-70° C.
b) Combine Mineral Oil, Stearyl Alcohol, Stearic Acid, White Petrolatum, Cetyl Alcohol and Microcrystalline Wax in beaker. Heat to 60-70° C. Add Carbopol 1382 and Pemulen TR-1. Mix to disperse.
c) Add the materials from step b) to step a) at 60-70° C. with rapid propeller mixing. Add Benzyl Alcohol and mix until smooth, homogeneous emulsion forms. Cool emulsion to about 40-45° C. while mixing. Disperse Calcipotriol into aqueous blend with homogenizing mixer. Add Calcipotriol dispersion to emulsion and mix. Continue mixing while cooling to room temperature.

EXAMPLE 16

Betamethasone Dipropionate Cream—useful for treating hand dermatitis, atopic eczema, and psoriasis

| COMPONENT | % w/w |
| --- | --- |
| Betamethasone Dipropionate, Micronized | 0.05 |
| White Wax | 3.0 |
| Stearic Acid | 3.0 |
| Stearyl Alcohol | 5.0 |
| Cetyl Alcohol | 1.0 |
| White Petrolatum | 10.0 |
| Carbomer 1382 | 0.2 |
| Pemulen TR-1 | 0.2 |
| Propylene Glycol | 10.0 |
| Ethoxydiglycol | 5.0 |
| Methylparaben | 0.2 |
| Propylparaben | 0.03 |
| Tromethamine (10% aqueous) | qs pH 5.5 |
| Purified Water | QSAD 100 | a) Combine and mix Purified Water, Tromethamine, Propylene Glycol and Sorbitol Solution in beaker. Heat to 60-70° C. Add Methylparaben and Propylparaben and mix until dissolved.
b) Combine Stearyl Alcohol, Stearic Acid, White Petrolatum, Cetyl Alcohol and Wax, White Wax in beaker. Heat to 60-70° C. Add Carbopol 1382 and Pemulen TR-1. Mix to disperse. Add the materials from step b) to step a) at 60-70° C. with rapid propeller mixing. Mix until smooth, homogeneous emulsion forms. Cool to about 45-50° C. while mixing Disperse Betamethasone Dipropionate into the Ethoxydiglycol with homogenizing mixer. Add Betamethasone Dipropionate dispersion to emulsion and mix well. Continue mixing while cooling to room temperature.

EXAMPLE 17

Skin Protectant Cream

| COMPONENT | % w/w |
| --- | --- |
| White Petrolatum (Active Ingredient) | 30.0 |
| Stearic Acid | 3.0 |
| Stearyl Alcohol | 5.0 |
| Cetyl Alcohol | 1.0 |

-continued

| COMPONENT | % w/w |
| --- | --- |
| Cholesterol | 0.2 |
| Pemulen TR-2 | 0.1 |
| Pemulen TR-1 | 0.2 |
| Glycerin | 4.0 |
| Benzyl Alcohol | 1.2 |
| Tromethamine (10% aqueous) | qs pH 5.0 |
| Purified Water | QSAD 100 | a) Combine and mix Purified Water, Tromethamine and Glycerin, in beaker. Heat to 60-70° C.
b) Combine Stearyl Alcohol, Stearic Acid, White Petrolatum, Cholesterol and Cetyl Alcohol in beaker. Heat to 60-70° C. Add Pemulen TR-2 and Pemulen TR-1. Mix to disperse.
c) Add the materials from step b) to step a) at 60-70° C. with rapid propeller mixing. Add Benzyl Alcohol and mix until smooth, homogeneous emulsion forms.
d) Continue mixing while cooling to room temperature.

EXAMPLE 18

Therapeutic Cream—for treating hand dermatitis and atopic dermatitis with the active ingredients being isopropyl myristate and sunflower seed oil

| COMPONENT | % w/w |
| --- | --- |
| Sunflower Seed Oil | 3.0 |
| Isopropyl myristate | 20.0 |
| Stearic Acid | 3.0 |
| Stearyl Alcohol | 5.0 |
| Cetyl Alcohol | 2.0 |
| Carbopol 1382 | 0.1 |
| Pemulen TR-1 | 0.2 |
| Glycerin | 6.0 |
| Sorbitol Solution, 70% | 3.0 |
| Tocopherol (Vitamin E) | 0.005 |
| Methylparaben | 0.2 |
| Propylparaben | 0.03 |
| Tromethamine | qs pH 5.0 |
| Purified Water | QSAD 100 | a) Combine Purified Water, Tromethamine, Glycerin and Sorbitol Solution in beaker. Add parabens and Sunflower Seed Oil. Heat to 60-70° C.
b) Combine Stearyl Alcohol, Cetyl Alcohol, Stearic Acid, Isopropyl myristate, and Tocopherol in beaker. Heat to 60-70° C. Add Carbopol 1382 and Pemulen TR-1. Mix to disperse.
c) Add the materials from step b) to step a) at 60-70° C. with rapid propeller mixing. Mix until smooth, homogeneous emulsion forms.
d) Continue mixing while cooling to room temperature.

EXAMPLE 19

| COMPONENT | % w/w |
| --- | --- |
| Isopropyl myristate (Active Ingredient) | 45.0 |
| Stearic Acid | 3.0 |
| Stearyl Alcohol | 5.0 |

-continued

| COMPONENT | % w/w |
|---|---|
| Cetyl Alcohol | 3.0 |
| Pemulen TR-2 | 0.1 |
| Pemulen TR-1 | 0.2 |
| Glycerin | 4.0 |
| Benzyl Alcohol | 1.2 |
| Tromethamine (10% aqueous) | qs pH 5-6 |
| Purified Water | QSAD 100 | a) Combine and mix Purified Water, Tromethamine and Glycerin, in beaker. Heat to 60-70° C.
b) Combine Stearyl Alcohol, Stearic Acid, Isopropyl Myristate, and Cetyl Alcohol in beaker. Heat to 60-70° C. Add Pemulen TR-2 and Pemulen TR-1. Mix to disperse.
c) Add the materials from step b) to step a) at 60-70° C. with rapid propeller mixing. Add Benzyl Alcohol and mix until smooth, homogeneous emulsion forms.
d) Continue mixing while cooling to room temperature.

EXAMPLE 20

The compositions as shown in Examples 2 and 4 were tested for irritation potential in an occlusive 46 hour human patch test using Finn Chambers® on Scanpor® (Allerderm Laboratories, Petaluma, Calif.). A side-by-side comparison was made to a commercial hand care lotion, Proteque (Proteque International, Inc., Raleigh, N.C.) and Retin A Gel (Ortho Pharmaceutical Corp., Raritan, N.J.), the positive control and a known skin irritant. Tests were performed for each product with duplicate patches on the right and left arm of the human test subject. The redness, induration, vessiculation, and other signs of irritation or inflammation, were scored at 19 and 32 hours by two observers, who were blind to the identity of the test sites. Scoring was according to the following scale:

| 0 = | No irritation |
|---|---|
| 1.0 = | Mild irritation |
| 2.0 = | Moderate irritation |
| 3.0 = | Severe irritation |

The following table summarizes the results based on the sum of two scorings of two test sites for each test material:

| Test Material | Score |
|---|---|
| Example 2 | 0 |
| Example 4 | 0 |
| Proteque Lotion | 2.0 |
| Retin A Gel, 0.025% | 11.5 |

The formulations of the invention according to Examples 2 and 4 showed no irritation. "Proteque" lotion induced measurable irritation with a score of 2.0 and Retin A gel had a near maximal score of 11.5 of a total possible score of 12.

EXAMPLE 22

An experiment was conducted to show latex glove compatibility of the emulsions of the invention as follows. The fingers of a latex glove were filled with about 10 ml of product and suspended in a glass jar. The latex was examined visually at hourly intervals for six hours, with one final evaluation, including dismantling the apparatus and palpation of the glove, conducted at 24 hours. No swelling, puckering, rupturing or discoloration was noted with the compositions of examples 2 and 4. By contrast, a positive control, mineral oil degraded the latex material after 24 hours of exposure causing rupture of the glove finger.

EXAMPLE 23

The composition described in Example 2 was tested for long-term stability in 2 ounce high density polyethylene tubes for up to 24 months. The physical appearance was monitored for compliance with the specification of "smooth off-white cream". both pH and viscosity were monitored during the study. pH was determined using a standardized pH meter and a 1:10 dilution of the cream in purified water. The viscosity was determined with a Brookfield viscometer using spindle 27 and a speed of one (1) RPM.

After one month of weekly cycling between freezer and ambient room temperature conditions, the product remained stable. Likewise, after 6 months at 30° C. and 24 months at 25° C. and 60% relative humidity, the product remained stable. The test results are summarized as follows:

| | Specification | Initial | 1 month freeze/ thaw cycling | 6 months at 30° C. | 24 months at 25°0 C./ 60% RH |
|---|---|---|---|---|---|
| Description | smooth, off-white cream | complies | complies | complies | complies |
| pH | 5.5 to 6.5 | 6.3 | 6.3 | 6.2 | 6.0 |
| Viscosity (centipoise) | 140,000 to 230,000 | 219,200 | 211,000 | 192,500 | 186,000 |

The emulsions and formulations of the invention provide multiple benefits to patients suffering from skin dermatoses and individuals prone to developing hand dermatoses. These benefits include, but are not limited to, providing lubricating topical drug delivery system that are free of low molecular weight surfactants. In this way, the emulsions of the invention promote healing and to not contribute further irritation of the dermatitic skin or mucous membrane disorders. Lotions and creams according to the invention provide lubrication and maintain an effective protective barrier against over drying on repeated hand washings. Further the emulsion of the invention, especially in a cream formulation, provides effective daytime protection and moisturization without inhibiting work performance due to the presence of a greasy base. Additionally, the use of emulsions, such as in examples 1 and 2, for hand care is compatible with concurrent latex glove use; this is particularly important for health care personnel.

The following U.S. patents are incorporated herein by reference: U.S. Pat. No. 5,004,598 (Lochhead), U.S. Pat. No. 5,928,632 (Reusch), U.S. Pat. No. 4,552,755 (Randen), U.S. Pat. No. 5,236,710 (Guerrero), U.S. Pat. No. 5,886,038 (Glenn).

While the foregoing has presented specific embodiments of the present invention, it is to be understood that these embodiments have been presented by way of example only. It is expected that others skilled in the art will perceive variations which, while varying from the foregoing, do not depart from the spirit and scope of the invention herein described and claimed.

The invention claimed is:

1. An emulsion for topical application to the skin comprising one or more acrylates/C10-C30 alkyl acrylate crosspolymer primary emulsifiers having a molecular weight of at least 100 kD, one or both of cetyl alcohol and stearyl alcohol, optionally a silicone oil at a concentration up to 0.5%, optionally cholesterol at a concentration up to 10%, and optionally stearic acid, wherein the emulsion contains an aqueous phase and an oil phase, wherein the oil phase constitutes 30% or less of the total formula weight of the emulsion and is free of materials other than silicones and triglycerides that are liquid at room temperature, and wherein the emulsion lacks any additional primary emulsifier having a molecular weight of less than 100 kD and is free of surface active film formers.

2. The emulsion of claim 1 wherein the oil phase constitutes 20% or less of the total formula weight of the emulsion.

3. The emulsion of claim 2 wherein the oil phase constitutes 15% or less of the total formula weight of the emulsion.

4. The emulsion of claim 1 which further comprises one or more of cholesterol at a concentration higher than 0.0%, a triglyceride containing one or more essential fatty acids, glycerin, and sorbitol.

5. The emulsion of claim 1 which comprises either or both of glycerin and sorbitol.

6. The emulsion of claim 1 which comprises cholesterol at a concentration higher than 0.0%.

7. The emulsion of claim 1 which comprises a triglyceride containing one or more essential fatty acids.

8. The emulsion of claim 1 which comprises cholesterol at a concentration higher than 0.0%, a triglyceride containing one or more essential fatty acids, and sorbitol.

9. The emulsion of claim 1 which is free of propylene glycol.

10. The emulsion of claim 1 which further comprises silicone oil at a concentration higher than 0.0%.

11. The emulsion of claim 1 which further comprises a pharmaceutically active ingredient.

12. The emulsion of claim 11 wherein the pharmaceutically active ingredient is a corticosteroid.

13. The emulsion of claim 11 wherein the pharmaceutically active ingredient is selected from the group consisting of isopropyl myristate, retinoic acid, benzoyl peroxide, a sunscreen, clindamycin, urea, metronidazole, miconazole, calcipotriol, hydrocortisone, and betamethasone.

14. The emulsion of claim 11 wherein the pharmaceutically active ingredient is metronidazole.

15. An emulsion for topical application to the skin comprising one or more acrylates/C10-C30 alkyl acrylate crosspolymer primary emulsifiers having a molecular weight of at least 100 kD, one or both of cetyl alcohol and stearyl alcohol, optionally a silicone oil at a concentration up to 0.5%, optionally cholesterol at a concentration up to 10%, and optionally stearic acid, wherein the emulsion contains an aqueous phase and an oil phase wherein the oil phase constitutes 30% or less of the total formula weight of the emulsion, wherein the emulsion lacks any additional primary emulsifier having a molecular weight of less than 100 kD and is free of surface active film formers, and wherein the emulsion does not break instantaneously upon contact with skin.

16. The emulsion of claim 15 wherein the emulsion does not break within the first 10 seconds of contact with skin.

17. The emulsion of claim 16 wherein the emulsion, when rubbed into the skin during the 10 seconds, does not break.

18. The emulsion of claim 15 wherein the emulsion does not break upon contact with the skin for one minute.

19. The emulsion of claim 15 wherein the oil phase of the emulsion is free of materials other than silicones and triglycerides that are liquid at room temperature.

20. The emulsion of claim 15 which is free of propylene glycol.

21. The emulsion of claim 15 which further comprises silicone oil at a concentration higher than 0.0%.

22. The emulsion of claim 15 which further comprises a pharmaceutically active ingredient.

23. The emulsion of claim 22 wherein the pharmaceutically active ingredient is a corticosteroid.

24. The emulsion of claim 22 wherein the pharmaceutically active ingredient is selected from the group consisting of isopropyl myristate, retinoic acid, benzoyl peroxide, a sunscreen, clindamycin, urea, metronidazole, miconazole, calcipotriol, hydrocortisone, and betamethasone.

25. The emulsion of claim 22 wherein the pharmaceutically active ingredient is metronidazole.

26. A method for treating skin or a mucous membrane comprising topically applying to the skin or to the mucous membrane an emulsion comprising one or more acrylates/C10-C30 alkyl acrylate crosspolymer primary emulsifiers having a molecular weight of at least 100 kD, one or both of cetyl alcohol and stearyl alcohol, optionally a silicone oil at a concentration up to 0.5%, optionally cholesterol at a concentration up to 10%, and optionally stearic acid, wherein the emulsion contains an aqueous phase and an oil phase, wherein the oil phase constitutes 30% or less of the total formula weight of the emulsion and is free of materials other than silicones and triglycerides that are liquid at room temperature, and wherein the emulsion lacks any additional primary emulsifier having a molecular weight of less than 100 kD and is free of surface active film formers.

27. The method of claim 26 wherein the emulsion does not break instantaneously upon contact with skin.

28. The method of claim 26 wherein the emulsion further comprises silicone oil at a concentration higher than 0.0%.

29. The emulsion of claim 26 wherein the emulsion further comprises a pharmaceutically active ingredient.

30. A method for treating skin or a mucous membrane comprising topically applying to the skin or to the mucous membrane an emulsion comprising one or more acrylates/C10-C30 alkyl acrylate crosspolymer primary emulsifiers having a molecular weight of at least 100 kD, one or both of cetyl alcohol and stearyl alcohol, optionally a silicone oil at a concentration up to 0.5%, optionally cholesterol at a concentration up to 10%, and optionally stearic acid, wherein the emulsion contains an aqueous phase and an oil phase wherein the oil phase constitutes 30% or less of the total formula weight of the emulsion, wherein the emulsion lacks any additional primary emulsifier having a molecular weight of less than 100 kD and is free of surface active film formers, and wherein the emulsion does not break instantaneously upon contact with skin.

31. The method of claim 30 wherein the emulsion does not break within the first 10 seconds of contact with skin.

32. The method of claim 31 wherein the emulsion, when rubbed into the skin during the 10 seconds, does not break.

33. The method of claim 30 wherein the emulsion does not break upon contact with the skin for one minute.

34. The method of claim 30 wherein the emulsion further comprises silicone oil at a concentration higher than 0.0%.

35. The method of claim 30 wherein the emulsion further comprises a pharmaceutically active ingredient.

36. The method of claim 30 wherein the emulsion is free of materials other than silicones and triglycerides that are liquid at room temperature.

37. The emulsion of claim 1 wherein the oil phase constitutes 30% or less of the total formula weight of the emulsion.

38. The emulsion of claim 15 wherein the oil phase constitutes 30% or less of the total formula weight of the emulsion.

39. The method of claim 26 wherein the oil phase constitutes 30% or less of the total formula weight of the emulsion.

40. The method of claim 30 wherein the oil phase constitutes 30% or less of the total formula weight of the emulsion.

41. The method of claim 26 wherein the skin or mucous membrane is irritated or afflicted with a disorder.

42. The method of claim 41 wherein the disorder is selected from the group consisting of hand dermatitis, eczema, atopic dermatitis, psoriasis, acne, rosacea, pruritus, and xerosis.

43. The method of claim 30 wherein the skin or mucous membrane is irritated or afflicted with a disorder.

44. The method of claim 43 wherein the disorder is selected from the group consisting of hand dermatitis, eczema, atopic dermatitis, psoriasis, acne, rosacea, pruritus, and xerosis.

45. The emulsion of claim 1 wherein the concentration of the acrylates/C10-C30 alkyl acrylate crosspolymer emulsifier is less than 0.5%.

46. The emulsion of claim 15 wherein the concentration of the acrylates/C10-C30 alkyl acrylate crosspolymer emulsifier is less than 0.5%.

47. A method for treating dermatitis comprising topically applying to skin afflicted with dermatitis an emulsion comprising one or more acrylates/C10-C30 alkyl acrylate crosspolymer primary emulsifiers having a molecular weight of at least 100 kD, one or both of cetyl alcohol and stearyl alcohol, optionally a silicone oil at a concentration up to 0.5%, optionally cholesterol at a concentration up to 10%, and optionally stearic acid, the oil phase constitutes 30% or less of the total formula weight of the emulsion and is free of materials other than silicones and triglycerides that are liquid at room temperature, and wherein the emulsion lacks any additional primary emulsifier having a molecular weight of less than 100 kD and is free of surface active film formers.

48. The method of claim 47 wherein the dermatitis is hand dermatitis.

49. A method for treating dermatitis comprising topically applying to skin afflicted with dermatitis an emulsion comprising one or more acrylates/C10-C30 alkyl acrylate crosspolymer primary emulsifiers having a molecular weight of at least 100 kD, one or both of cetyl alcohol and stearyl alcohol, optionally a silicone oil at a concentration up to 0.5%, optionally cholesterol at a concentration up to 10%, and optionally stearic acid, wherein the emulsion contains an aqueous phase and an oil phase wherein the oil phase constitutes 30% or less of the total formula weight of the emulsion, wherein the emulsion lacks any additional primary emulsifier having a molecular weight of less than 100 kD and is free of surface active film formers, and wherein the emulsion does not break instantaneously upon contact with skin.

50. The method of claim 49 wherein the dermatitis is hand dermatitis.

* * * * *